(12) United States Patent
Kodera

(10) Patent No.: US 12,304,886 B2
(45) Date of Patent: May 20, 2025

(54) COMPOSITION FOR RESIN RAW MATERIAL

(71) Applicant: HONSHU CHEMICAL INDUSTRY CO., LTD., Tokyo (JP)

(72) Inventor: Masato Kodera, Wakayama (JP)

(73) Assignee: HONSHU CHEMICAL INDUSTRY CO., LTD., Tokyo (JP)

( * ) Notice: Subject to any disclaimer, the term of this patent is extended or adjusted under 35 U.S.C. 154(b) by 536 days.

(21) Appl. No.: 17/776,118

(22) PCT Filed: Nov. 26, 2020

(86) PCT No.: PCT/JP2020/044038
§ 371 (c)(1),
(2) Date: May 11, 2022

(87) PCT Pub. No.: WO2021/107017
PCT Pub. Date: Jun. 3, 2021

(65) Prior Publication Data
US 2022/0396544 A1    Dec. 15, 2022

(30) Foreign Application Priority Data
Nov. 29, 2019   (JP) .................. 2019-216305

(51) Int. Cl.
*C07C 59/31*    (2006.01)
(52) U.S. Cl.
CPC .......... *C07C 59/31* (2013.01); *C07C 2602/10* (2017.05)
(58) Field of Classification Search
CPC .... C07C 59/31; C07C 2602/10; C08G 63/668
USPC ...................................................... 563/466
See application file for complete search history.

(56) References Cited

U.S. PATENT DOCUMENTS

| | | | |
|---|---|---|---|
| 2022/0380286 A1 | 12/2022 | Sakuma et al. | |
| 2023/0002300 A1 | 1/2023 | Sakuma et al. | |

FOREIGN PATENT DOCUMENTS

| | | | |
|---|---|---|---|
| EP | 3805195 A1 | 4/2021 | |
| EP | 4001251 B1 | 11/2024 | |
| JP | 2001072872 A | 3/2001 | |
| JP | 2008024650 A | 2/2008 | |
| JP | 2018002893 A | 1/2018 | |
| JP | 2018002894 A | 1/2018 | |
| JP | 2018002895 A | 1/2018 | |
| JP | 007295692 B2 | 6/2023 | |
| KR | 20220006509 A | 1/2022 | |
| WO | 2019230685 A1 | 12/2019 | |
| WO | 2020226114 A1 | 11/2020 | |
| WO | 2021010363 A1 | 1/2021 | |

OTHER PUBLICATIONS

International Search Report (ISR) mailed Jan. 12, 2021, issued for International application No. PCT/JP2020/044038. (3 pages).
Lehn et al., Synthesis and properties of chiral macrotricyclic ligands. Complexation and transport of chiral molecular cations and anions, Helvetica Chimica Acta, 1978, pp. 2407-2418, vol. 61, No. 7. (12 pages).
International Preliminary Report on Patentability, dated May 17, 2022, for corresponding international application PCT/JP2020/044038 (1 page).
Notification Concerning Transmittal of International Preliminary Report on Patentability, mailed Jun. 9, 2022, for corresponding international application PCT/JP2020/044038 (1 page).

(Continued)

*Primary Examiner* — Ana Z Muresan
(74) *Attorney, Agent, or Firm* — Law Office of Katsuhiro Arai

(57) ABSTRACT

In order to improve resin physical properties such as heat resistance (glass transition temperature) of a resin such as polyester obtained from 2,2'-bis(carboxymethoxy)-1,1'-binaphthyl, provided is a composition for a resin raw material containing a compound represented by formula (1) as a component A and a compound represented by formula (2) as a component B, wherein their composition ratios are in ranges wherein the component A is present in an amount of 98.0 area % or more and 99.99 area % or less, and the component B is present in an amount of 1.50 area % or less, relative to the total amount of all components detected at a wavelength of 280 nm by high-performance liquid chromatography analysis using a UV detector.

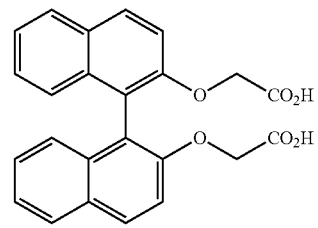

(1)

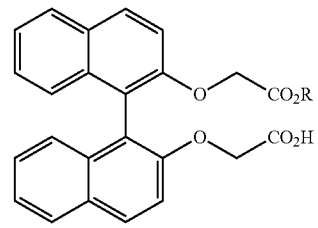

(2)

1 Claim, No Drawings

(56) References Cited

OTHER PUBLICATIONS

Notification of Transmittal of Translation of the International Preliminary Report on Patentability, mailed Jun. 9, 2022, for corresponding international application PCT/JP2020/044038 (1 page).
Written Opinion of the International Searching Authority, mailed Jan. 12, 2021, for corresponding international application PCT/JP2020/044038 (4 page).

COMPOSITION FOR RESIN RAW MATERIAL

CROSS-REFERENCE TO RELATED APPLICATIONS

This application is the U.S. National Phase under 35 U.S.C. § 371 of International Application PCT/JP2020/044038, filed Nov. 26, 2020, which claims priority to Japanese Patent Application No. JP2019-216305, filed Nov. 29, 2019. The International Application was published under PCT Article 21(2) in a language other than English.

TECHNICAL FIELD

The present invention relates to a composition for a resin raw material, the composition being composed mainly of 2,2'-bis(carboxymethoxy)-1,1'-binaphthyl.

BACKGROUND ART

Polyester resins and polyester carbonate resins produced using dicarboxylic acid components having a binaphthalene skeleton as polymerization components have excellent optical properties such as high refractive indices and low birefringence and have high levels of heat resistance, and thus have recently been expected to be materials for optical members such as optical disks, transparent conductive substrates, and optical filters. In particular, resins produced using 2,2'-bis(carboxymethoxy)-1,1'-binaphthyl, which has a chemical structure represented by a chemical formula below, as a polymerization component have been attracting attention for their particularly excellent optical properties (see, for example, PTLs 1 to 3).

[Chem. 1]

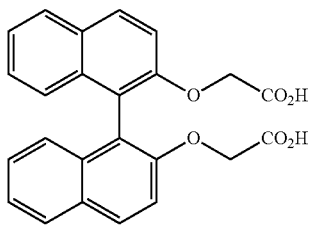

Known methods for producing 2,2'-bis(carboxymethoxy)-1,1'-binaphthyl represented by the chemical formula above include reaction of 1,1'-binaphthalene-2,2'-diol with a halogenated acetate ester, as shown by reaction formula 1 below, and reaction of 1,1'-binaphthalene-2,2'-diol with a halogenated acetic acid, as shown by reaction formula 2 below.

<Reaction Formula 1>

[Chem. 2]

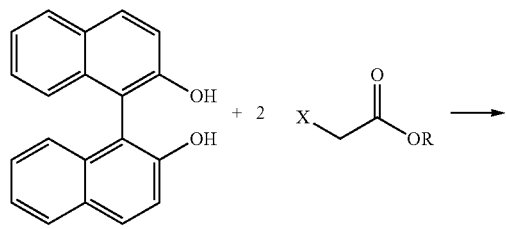

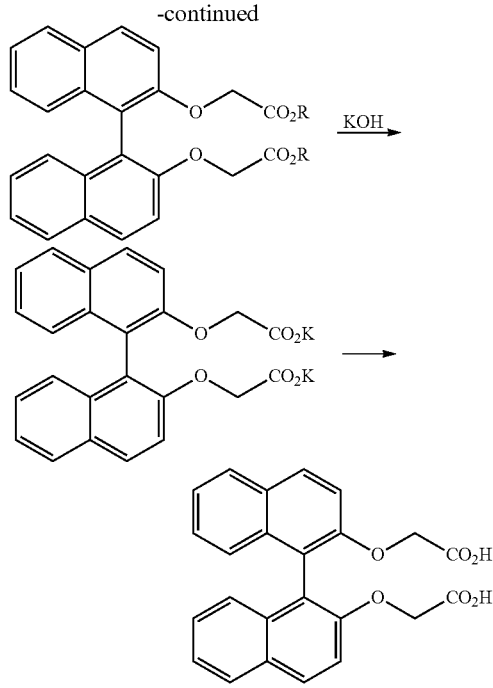

<Reaction Formula 2>

[Chem. 3]

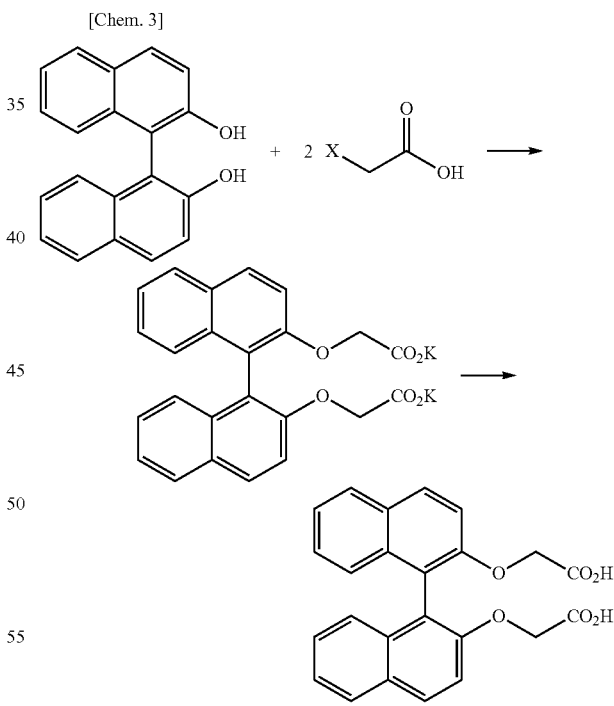

However, the present inventors have found that the production method represented by reaction formula 1 above has a problem in that due to the presence of a halogenated acetate ester-derived alcohol (ROH) produced after hydrolysis, a carboxylic acid of 2,2'-bis(carboxymethoxy)-1,1'-binaphthyl reacts with the alcohol to produce an ester as a by-product, and when a resin is produced using the resulting product, the resin has insufficient heat resistance.

In addition, the production method represented by reaction formula 2 above has a problem in that a large amount of by-products are produced during the etherification reaction, which makes purification very difficult, and a high-performance resin raw material cannot be formed.

Under these circumstances, there has been a demand for a resin raw material that can provide a resin excellent in resin physical properties such as heat resistance. In optical applications, it is important and significant to obtain a resin with a good hue, and thus a resin raw material therefor has also been demanded.

CITATION LIST

Patent Literature

PTL 1: Japanese Unexamined Patent Application Publication No. 2018-002893
PTL 2: Japanese Unexamined Patent Application Publication No. 2018-002894
PTL 3: Japanese Unexamined Patent Application Publication No. 2018-002895

SUMMARY OF INVENTION

Technical Problem

The present invention has been made in view of the foregoing circumstances, and an object thereof is to improve resin physical properties such as heat resistance (glass transition temperature) of a resin such as polyester obtained from 2,2'-bis(carboxymethoxy)-1,1'-binaphthyl.

Solution to Problem

To achieve the above object, the present inventors have conducted intensive studies and found that when a resin raw material composed mainly of 2,2'-bis(carboxymethoxy)-1,1'-binaphthyl contains a monoester, which is a by-product, in a range below a specific amount, resin physical properties such as heat resistance (glass transition temperature) are improved, thereby completing the present invention.

The present invention is as follows.
1. A composition for a resin raw material, characterized by comprising:
   a compound represented by formula (1) below as a component A, and
   a compound represented by formula (2) below as a component B; and
   having its composition ratio in a range below.
[Composition ratio]: The component A is present in an amount of 98.0 area % or more and 99.99 area % or less, and the component B is present in an amount of 1.50 area % or less, relative to the total amount of all components detected at a wavelength of 280 nm by high-performance liquid chromatography analysis using a UV detector.

[Chem.4]

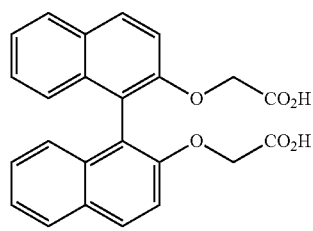

(1)

[Chem. 5]

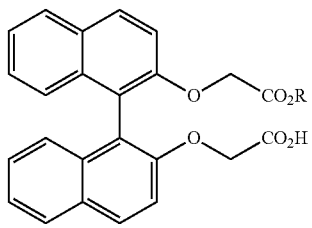

(2)

(In the formula, R represents an alkyl group having 1 to 8 carbon atoms or an aryl group having 6 to 12 carbon atoms.)

Advantageous Effects of Invention

If the composition for a resin raw material according to the present invention is used, a resin having greatly improved resin physical properties such as heat resistance (glass transition temperature) is obtained, which is useful.

In addition, if the composition for a resin raw material according to the present invention is used, a resin also having an excellent hue can be obtained in a stable manner, which is advantageous also from an industrial point of view.

That is, the provision of the composition for a resin raw material according to the present invention is very useful in that a resin having excellent resin physical properties such as heat resistance and having a good hue can be obtained in an industrially stable manner.

DESCRIPTION OF EMBODIMENTS

Hereinafter, the present invention will be described in detail.

The present invention relates to a composition for a resin raw material, the composition being composed mainly of 2,2'-bis(carboxymethoxy)-1,1'-binaphthyl, which is a component A, and containing a component B in a very small amount. For the composition ratio of the components A and B, the component A is present in an amount of 98.0 area % or more and 99.99 area % or less, and the component B is present in an amount of 1.50 area % or less, relative to the total amount of all components detected at a wavelength of 280 nm by high-performance liquid chromatography analysis using a UV detector. In this composition ratio, the lower limit of the component B is not zero, and the composition for a resin raw material according to the present invention necessarily contains the component B, although in a very small amount.

Here, the presence of the component B in the composition for a resin raw material according to the present invention can be confirmed by increasing a sample concentration in high-performance liquid chromatography analysis using a UV detector, as will be described in detail in EXAMPLES, or by NMR.

<Component A>

The composition for a resin raw material according to the present invention mainly contains 2,2'-bis(carboxymethoxy)-1,1'-binaphthyl represented by formula (1) below as the component A.

The content of the component A in the composition for a resin raw material according to the present invention is 98.0 area % or more and 99.99 area % or less relative to the total amount of all components detected at a wavelength of 280 nm by high-performance liquid chromatography analysis using a UV detector. The lower limit thereof is preferably 99.0 area % or more, more preferably 99.5 area % or more, still more preferably 99.7 area % or more, particularly preferably 99.8 area % or more.

[Chem. 6]

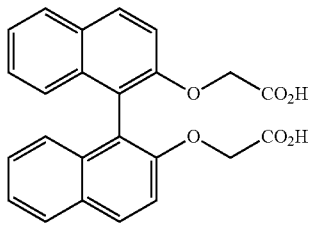

(1)

<Component B>

The composition for a resin raw material according to the present invention contains, as the component B, a compound represented by formula (2) below in the range of 1.50 area % or less relative to the total amount of all components detected at a wavelength of 280 nm by high-performance liquid chromatography analysis using a UV detector. The upper limit thereof is preferably 1.00 area % or less, more preferably 0.50 area % or less, still more preferably 0.20 area % or less, particularly preferably 0.10 area % or less. The lower limit thereof is not zero, and the composition for a resin raw material according to the present invention contains a minimal amount of the component B. From an economical point of view, the component B is present preferably in an amount of 0.01 area % or more, more preferably in an amount of 0.02 area % or more, particularly preferably in an amount of 0.03 area % or more.

A resin obtained using a composition for a resin raw material containing the compound represented by formula (2) below in an amount of more than 1.50 area % has low heat resistance and presents problems in industrial applications.

[Chem. 7]

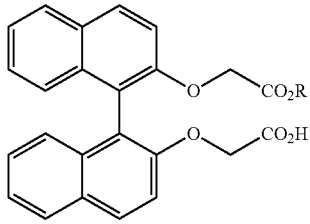

(2)

(In the formula, R represents an alkyl group having 1 to 8 carbon atoms or an aryl group having 6 to 12 carbon atoms.)

"R" in formula (2) above is an alkyl group having 1 to 8 carbon atoms or an aryl group having 6 to 12 carbon atoms. Specific examples of the alkyl group having 1 to 8 carbon atoms include linear alkyl groups such as a methyl group, an ethyl group, and a n-propyl group, and branched alkyl groups in which carbon bonded to an oxygen atom is primary or secondary carbon, such as an i-propyl group and an i-butyl group. Among them, linear alkyl groups are preferred. Specific examples of the aryl group having 6 to 12 carbon atoms include a phenyl group, a methylphenyl group, an ethylphenyl group, a xylyl group, a trimethylphenyl group, a tetramethylphenyl group, a biphenyl group, and a naphthyl group. "R" in formula (2) above is preferably an alkyl group having 1 to 8 carbon atoms.

<Method for Producing Composition for Resin Raw Material>

A method for producing the composition for a resin raw material according to the present invention will be described below.

The composition for a resin raw material according to the present invention can be obtained by a production method represented by reaction formula A below. Specifically, the composition for a resin raw material according to the present invention containing the component B of the present invention in a very small amount can be obtained in such a manner that after a hydrolysis reaction of a diester represented by formula (a) below, an ester-derived alcohol represented by formula (b) below is distilled off from the reaction system, then the reaction solution is acidified, and 2,2'-bis(carboxymethoxy)-1,1'-binaphthyl is precipitated in the presence of an organic solvent.

<Reaction formula A>

[Chem. 8]

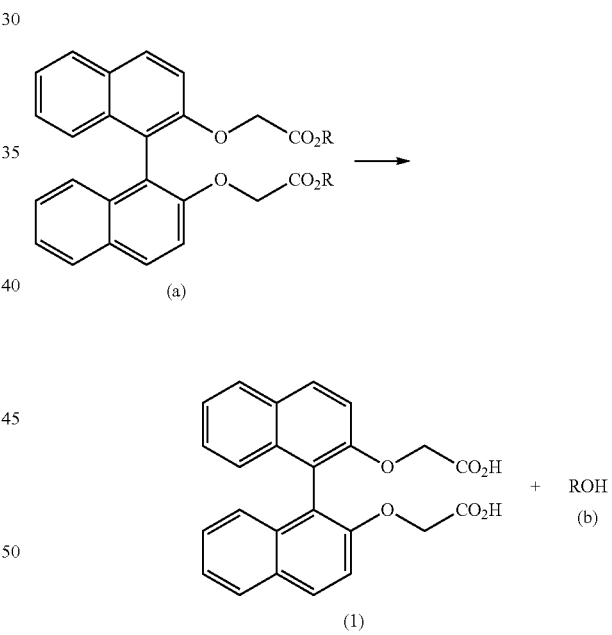

(In the formula, R represents an alkyl group having 1 to 8 carbon atoms or an aryl group having 6 to 12 carbon atoms.)

"R" in formula (a) and formula (b) above is the same as "R" in formula (2) above, and specific examples and preferred examples thereof are also the same.

<Reaction Method for Obtaining Diester Represented by Formula (a)>

The diester represented by formula (a) can be obtained by reacting 1,1'-binaphthalene-2,2'-diol with a halogenated acetate ester represented by formula (c) below, as represented by the following reaction formula.

[Chem.9]

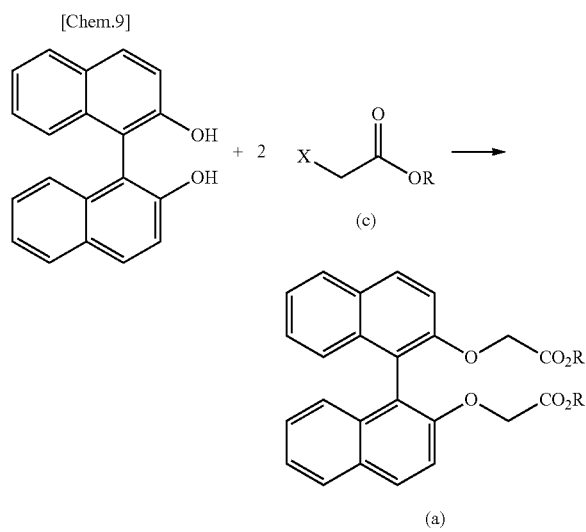

(In the formula, R represents an alkyl group having 1 to 8 carbon atoms or an aryl group having 6 to 12 carbon atoms.)

"R" in formula (c) above is the same as "R" in formula (2) above, and specific examples and preferred examples thereof are also the same. "X" in formula (c) is a halogen atom, preferably a chlorine atom, a bromine atom, or an iodine atom.

In the synthesis of the diester represented by formula (a), two or more halogenated acetate esters represented by formula (c) with different alkyl ester moieties may be used in combination, but for simple and easy purification, it is preferable to use a single halogenated acetate ester represented by formula (c). The amount of the halogenated acetate ester represented by formula (c) used is not particularly limited as long as the molar ratio of the halogenated acetate ester to 1,1'-binaphthalene-2,2'-diol is more than or equal to a theoretical value (2.0), and the halogenated acetate ester is used typically in an amount of 2 mol or more, preferably in an amount of 2.1 to 3.0 mol, more preferably in an amount of 2.2 to 2.8 mol.

(Reaction Solvent)

The synthesis of the diester represented by formula (a) above may be performed without a reaction solvent but is preferably performed using a reaction solvent for reasons of, for example, ease of operation in industrial production and improvement in reaction rate. The reaction solvent is not particularly limited as long as it is not distilled out of a reaction vessel at a reaction temperature and is inactive in the reaction, and examples include linear or cyclic ketone solvents having 5 to 8 carbon atoms, such as diethyl ketone, methyl isobutyl ketone, methyl amyl ketone, 2-octanone, cyclopentanone, and cyclohexanone, and linear nitrile solvents having 2 to 6 carbon atoms, such as acetonitrile and propanenitrile. These reaction solvents may be used alone or may be used in an appropriate combination of two or more to adjust polarity. In particular, methyl isobutyl ketone and acetonitrile are preferred. The amount of reaction solvent used is preferably in the range of 150 to 500 parts by weight, more preferably in the range of 200 to 300 parts by weight, relative to 100 parts by weight of 1,1'-binaphthalene-2,2'-diol.

(Base)

In the synthesis of the diester represented by formula (a) above, 1,1'-binaphthalene-2,2'-diol is preferably formed into a salt with a base before being reacted with the halogenated acetate ester represented by formula (c) above. The base is not particularly limited, and, for example, alkali metal carbonates such as lithium carbonate, sodium carbonate, and potassium carbonate; alkali metal hydrogen carbonates such as sodium hydrogen carbonate and potassium hydrogen carbonate; alkali metal hydroxides such as lithium hydroxide, sodium hydroxide, and potassium hydroxide; and organic bases such as triethylamine and pyridine are suitable for use. These may be used alone or as a mixture of two or more. In particular, sodium carbonate and potassium carbonate are preferred.

The amount of base used is preferably 2.0 to 2.5 mol, more preferably 2.05 to 2.15 mol, relative to 1 mol of 1,1'-binaphthalene-2,2'-diol.

(Alkali metal iodide)

In the synthesis of the diester represented by formula (a) above, the reaction may be carried out in the presence of an alkali metal iodide. Specific examples of the alkali metal iodide include potassium iodide, sodium iodide, cesium iodide, and lithium iodide. These may be used alone or as a mixture of two or more.

The amount of alkali metal iodide used is preferably in the range of 1 to 25 mol %, more preferably in the range of 2 to 15 mol %, still more preferably in the range of 2.5 to 10 mol %, particularly preferably in the range of 3 to 5 mol %, relative to 1 mol of 1,1'-binaphthalene-2,2'-diol.

(Reaction Temperature and Pressure)

The reaction temperature is typically 50° C. to 150° C., preferably in the range of 70° C. to 130° C., more preferably in the range of 90° C. to 110° C. A high reaction temperature is not preferred because the yield decreases due to, for example, hydrolysis of the resulting diester represented by formula (a) above, and a low reaction temperature is not preferred because the reaction rate slows down. The reaction is typically carried out under normal pressure, but depending on the boiling point of an organic solvent used, the reaction may be carried out under increased pressure or reduced pressure so that the reaction temperature falls within the above range.

(Reaction Endpoint)

The endpoint of the reaction can be determined by liquid chromatography or gas chromatography analysis. The endpoint of the reaction is preferably defined as the time point at which unreacted 1,1'-binaphthalene-2,2'-diol has disappeared and the increase of the diester represented by formula (a) above is no longer observed. Although the reaction time varies depending on the reaction conditions such as reaction temperature, the reaction is typically completed in about 1 to 30 hours.

After completion of the reaction, water is added to the reaction solution, the mixture is stirred, and the resultant is then left to stand to separate an aqueous layer. This water washing operation is performed twice or more, whereby the inorganic salt in the reaction solution can be removed. The amount of water used in one water washing operation is preferably in the range of 150 to 600 parts by weight, more preferably in the range of 200 to 400 parts by weight, relative to 100 parts by weight of 1,1'-binaphthalene-2,2'-diol used, and the temperature in the operation is preferably in the range of 60° C. to 100° C., more preferably in the range of 70° C. to 90° C. The stirring may be performed in any manner as long as an oil layer is sufficiently brought into contact with an aqueous layer, and although the time required varies depending on the apparatus, about 30 minutes usually suffices.

<Hydrolysis Reaction>
(Reaction Solvent)

The hydrolysis reaction in reaction formula A can be carried out using a solution that has been through the water washing operation after completion of the synthesis reaction of the diester represented by formula (a) above. When the hydrolysis reaction is carried out using the purified diester represented by formula (a) above, it is preferable to use, as a reaction solvent, a mixed solvent of an organic solvent and water. Specific examples of the organic solvent used include linear or cyclic ketone solvents having 5 to 8 carbon atoms, such as diethyl ketone, methyl isobutyl ketone, methyl amyl ketone, 2-octanone, cyclopentanone, and cyclohexanone, and linear nitrile solvents having 2 to 6 carbon atoms, such as acetonitrile and propanenitrile. The amount of organic solvent used is preferably 100 to 600 parts by weight, more preferably 130 to 400 parts by weight, relative to 100 parts by weight of the diester represented by formula (a) above. The amount of water used is preferably 10 to 200 parts by weight, more preferably 20 to 150 parts by weight, relative to 100 parts by weight of the diester represented by formula (a) above.

(Base)

To hydrolyze the diester represented by formula (a) above, a base is used. Specific examples of the base used include alkali metal hydroxides such as lithium hydroxide, sodium hydroxide, and potassium hydroxide. The base may be used as a solid or in the form of an aqueous solution. The concentration of the base used in the form of an aqueous solution is preferably 10 to 60 wt %, more preferably 20 to 50 wt %.

The amount of the base used is preferably 2.0 to 6.0 mol, more preferably 2.5 to 4.0 mol, relative to 1 mol of the diester represented by formula (a) above.

(Reaction Temperature)

The reaction temperature is typically 30° C. to 100° C., preferably in the range of 50° C. to 90° C., more preferably in the range of 60° C. to 80° C., and it is preferable to add or drop the above base or an aqueous solution thereof while maintain this temperature.

The reaction is typically completed in about 1 to 10 hours.

<Method of Distilling Off Resulting Alcohol Represented by Formula (b) From Reaction System>

The method for producing the composition for a resin raw material according to the present invention preferably includes, after the above hydrolysis reaction, a step of distilling off an alcohol resulting from the hydrolysis reaction and represented by formula (b) from the reaction system.

(Temperature)

The temperature at which the alcohol represented by formula (b) above is distilled off from the reaction system is preferably in the range of 40° C. to 130° C., more preferably in the range of 60° C. to 100° C., still more preferably in the range of 70° C. to 90° C.

(Pressure)

The pressure at which the alcohol represented by formula (b) above is distilled off from the reaction system may be normal pressure or reduced pressure, and when the distillation is performed on an industrial scale, it is preferably performed under reduced pressure because the solvent can be distilled out more efficiently.

(Solvent)

When the alcohol represented by formula (b) above is distilled off from the reaction system, an organic solvent may be added to the reaction system as needed. Examples of the solvent added include linear ketone solvents having a total of 5 to 8 carbon atoms, such as diethyl ketone, methyl isobutyl ketone, methyl amyl ketone, methyl hexyl ketone, and 2-octanone.

(Distillation Quantity)

In distilling off the alcohol represented by formula (b) above from the reaction system, the distillation quantity of the alcohol and the organic solvent added to the reaction system as needed is preferably in the range of 150 to 450 parts by weight, more preferably 200 to 300 parts by weight, relative to 100 parts by weight of the diester represented by formula (a) above.

<Method of Acidifying Reaction Solution>

In the method for producing the composition for a resin raw material according to the present invention, after the step of distilling off the alcohol represented by formula (b) above from the reaction system, the reaction solution is preferably acidified. Specific examples of an acid used in acidifying the reaction solution include hydrogen chloride, hydrogen bromide, inorganic acids such as sulfuric acid, and organic acids such as p-toluenesulfonic acid, methanesulfonic acid, and trifluoromethanesulfonic acid. The amount of acid used is preferably 2.2 to 4.0 mol, more preferably 2.5 to 3.0 mol, relative to 1 mol of the diester represented by formula (a) above.

When concentrated hydrochloric acid is used as the acid, the amount thereof in terms of hydrogen chloride is preferably 2.2 to 4.0 mol, more preferably 2.5 to 3.0 mol, relative to 1 mol of the diester represented by formula (a) above.

Specific examples of a solvent used in acidifying the reaction solution include linear or cyclic ketone solvents having 5 to 8 carbon atoms, such as diethyl ketone, methyl isobutyl ketone, methyl amyl ketone, 2-octanone, cyclopentanone, and cyclohexanone. The amount of reaction solvent used is preferably 250 to 1050 parts by weight, more preferably 350 to 900 parts by weight, relative to 100 parts by weight of the diester represented by formula (a) above.

<Method of Precipitating Component A in Presence of Organic Solvent>

In the method for producing the composition for a resin raw material according to the present invention, it is preferable to precipitate the component A in the presence of an organic solvent after the above reaction solution is acidified. After the above reaction solution is acidified, the reaction solution is preferably washed with water before the component A is precipitated. More preferably, the reaction solution is washed with water once to multiple times to the extent that an aqueous layer left after the water washing operation becomes neutral to slightly acidic.

(Solvent)

The precipitation of the component A is preferably carried out in the presence of at least an organic solvent. The precipitation may be carried out not only in the presence of an organic solvent but also in the presence of a mixture of an organic solvent and water, and, in particular, it is preferable to precipitate the component A in the presence of a mixed solvent of water and (a) at least one selected from linear ketone solvents having a total of 5 to 8 carbon atoms, (b) at least one selected from cyclic ketone solvents having a total of 5 to 8 carbon atoms, (c) at least one selected from cyclic ether solvents having a total of 4 to 8 carbon atoms, (d) at least one selected from cyclic ester solvents having a total of 4 to 8 carbon atoms, or (e) at least one selected from linear ketone solvents having a total of 3 to 8 carbon atoms or in the presence of any of these solvents (a) to (e). Of these, methyl isobutyl ketone, methyl amyl ketone, and 2-octanone, which have low water solubility, are suitable, and the amount of linear ketone solvent used to dissolve the component A is preferably 250 to 1000 parts by weight, more preferably 300 to 800 parts by weight, still more preferably 400 to 600 parts by weight, relative to 100 parts by weight of the component A contained in crystals or a solution used. The amount of cyclic ketone solvent, cyclic ether solvent, or cyclic ester solvent used to dissolve the component A is preferably 50 to 600 parts by weight, more preferably 50 to 400 parts by weight, still more preferably 100 to 200 parts by weight, relative to 100 parts by weight of the component A contained in crystals or a solution used.

(Temperature)

The temperature at which the component A is precipitated, for example, in the case where methyl isobutyl ketone, methyl amyl ketone, 2-octanone, or the like is used is preferably 90° C. to 130° C., more preferably 95° C. to 105° C.

A solution obtained by dissolving the component A in an organic solvent may be cooled as it is to precipitate the component A, or crystals may be precipitated while distilling out the organic solvent from the solution by distillation. The time spent on solvent distillation is preferably 2 to 15 hours, more preferably 4 to 10 hours, still more preferably 6 to 8 hours.

In the step of precipitating the component A, it is preferable to perform cooling after crystals are precipitated or while precipitating crystals, and the rate of the cooling is preferably 5° C. to 15° C. per hour, more preferably 7° C. to 12° C. per hour. In precipitating crystals, seed crystals need not be used but are preferably used, and crystals precipitated without seed crystals may be used as seed crystals. The final cooling temperature is preferably 20° C. to 60° C., more preferably 25° C. to 35° C. After cooling to this temperature, precipitated crystals are separated by filtration.

The crystals obtained can optionally be recrystallized under the same conditions to obtain the composition for a resin raw material in which the content of the component B is small.

<Drying>

In the method for producing the composition for a resin raw material according to the present invention, the crystals obtained by the precipitation of the component A is preferably dried. By drying the crystals, the solvent used in precipitating the component A can be removed. This drying can be performed by drying the crystals obtained by crystallization preferably under reduced pressure at 60° C. to 120° C., more preferably under reduced pressure at 70° C. to 110° C. The drying may be performed under normal pressure or reduced pressure. When the drying is performed on an industrial scale, it is preferably performed under reduced pressure because the solvent used in precipitating the component A can be removed more efficiently.

<Composition for Resin Raw Material>

The type of resin produced using the composition for a resin raw material according to the present invention is not particularly limited, and a polyester resin or a polyester carbonate resin is suitable. These resins may have any structure among random, block, and alternating copolymers. When a polyester resin, a polyester carbonate resin, or the like is produced, a known aliphatic and/or aromatic diol can be used, and any other dicarboxylic acid can be used in combination as long as the advantageous effects of the present application are not impaired.

EXAMPLES

The present invention will now be described more specifically with reference to Examples, but it should be noted that the present invention is not limited to these Examples.

The method of analysis is as follows.

<Method of Analysis>

1. Method of Determining Composition Ratio in Present Invention of Component A and Component B of Present Invention The composition ratio in the present invention of the component A and the component B in each of the compositions for resin raw materials obtained in Examples and Comparative Examples was determined by performing high-performance liquid chromatography analysis under the following conditions.

(1) Analysis Apparatus and Analysis Conditions

Measuring apparatus: high-performance liquid chromatography analyzer (UFLC) (manufactured by Shimadzu Corporation)

Pump: LC-20AD Column oven: CTO-20A Detector: SPD-20A (UFLC); cell length, 5 mm Column: HALO-C18 (column, 3.0×75 mm; particle size, 2.7 μm; manufactured by Advanced Materials Technology)

Oven temperature: 50° C.

Flow rate: 0.7 ml/min

Mobile phase: (A) acetonitrile, (B) 0.1 vol % aqueous phosphoric acid solution

Gradient conditions: (A) volume % (time from start of analysis)

30% (0 min)→100% (12 min)→100% (15 min)

Detection wavelength: 280 nm

Sample concentration: 0.8 mg/ml

Sample injection volume: 5 μl (2) Method of Determining "All Components" in Present Invention All components detected at a wavelength of 280 nm by high-performance liquid chromatography analysis using a UV detector in the present invention mean components determined to have "peaks" containing impurities, with waveform processing and a minimum peak area set as follows.

Waveform processing parameter: width, 5 sec or more; slope, 200 μV/min or more

Minimum peak area: 0.006% or more relative to peak area of component A (3) Method of Determining Composition ratio in Present Invention The composition ratio was determined from the ratios of peak areas of the component A and the component B to the total peak area of the "all components" determined by (2) above.

2. Method of Confirming Presence of Component B of Present Invention

By performing high-performance liquid chromatography analysis with only the sample concentration among the analysis conditions in (1) above changed to "10 mg/ml", the presence of the component (B) can be confirmed even in the composition for a resin raw material according to the present invention in which the content of the component (B) is less than the detection limit under the analysis conditions in 1. (1) above.

A sample with a sample concentration of 10 mg/ml can be prepared as follows: 500 mg of a composition for a resin raw material containing the component A and the component B is accurately weighed; a mixed solvent of about 40 ml of acetonitrile and about 1 g of water is added to dissolve the composition for a resin raw material; and acetonitrile is added to the solution to a total amount of 50 ml.

3. Analysis Method in Resin Performance Evaluation Test (1) The analysis of weight-average molecular weights was performed by the following gel permeation chromatography measurement.

Apparatus: HLC-8320GPC manufactured by Tosoh Corporation
Flow rate: 0.35 ml/min
Mobile phase: tetrahydrofuran
Injection volume: 20 µl
Column: TSKgel guardcolumn SuperMP(HZ)-N, three TSKgel SuperMultiporeHZ-N columns
Detector: RI
Analysis method: relative molecular weight in terms of polystyrene As polystyrene standards, A-500, A-2500, A-5000, F-1, F-2, and F-4 manufactured by Tosoh Corporation were used.

(2) Glass transition temperatures (Tg) were each measured using either of the following differential scanning calorimeters in such a manner that a measurement sample was heated to 300° C. under a stream of nitrogen, then cooled, and heated again under the following conditions.

Apparatus: Examples 1 and 2 and Comparative Examples 1 and 2: DSC-60 (manufactured by Shimadzu Corporation)
Examples 3 and 4 and Comparative Examples 3 to 6: DSC7020 (manufactured by Hitachi High-Tech Science Corporation)
Amount of measurement sample: 7 to 10 mg
Heating rate: 10° C./min (30° C. to 110° C.)
Nitrogen flow rate: 50 ml/min (3) Hues were measured with the following colorimeter.

Measuring instrument: TZ 6000 manufactured by Nippon Denshoku Industries Co., Ltd.

After "standard calibration" of the above measuring instrument was performed using distilled water, the melt color of a resin in a molten state was measured.

EXAMPLE 1

In a container equipped with a stirrer, 100 parts by weight of 1,1'-binaphthalene-2,2'-diol, 150 parts by weight of methyl isobutyl ketone, 101 parts by weight of potassium carbonate, and 2.1 parts by weight of potassium iodide were placed, heated to 90° C., and stirred at a temperature of 90° C. to 100° C. for one hour. After a mixed solution of 94 parts by weight of ethyl chloroacetate and 1 part by weight of N-methylpyrrolidone was prepared, the mixed solution was added dropwise while maintaining the temperature of the reaction solution at 90° C. to 102° C. After stirring for 10 hours, 400 parts by weight of water was added, and the resulting mixture was stirred at 80° C. to 85° C. and then left to stand to remove an aqueous layer. Subsequently, after 300 parts by weight of methyl isobutyl ketone was added to the resulting oil layer, 87.4 parts by weight of a 48% aqueous potassium hydroxide solution was added dropwise while maintaining the reaction solution temperature at 80° C. to 85° C.

After completion of the dropwise addition, stirring was performed at 80° C. to 85° C. for two hours, and 400 parts by weight of methyl isobutyl ketone was added to the reaction solution. While maintaining the temperature of the reaction solution at 75° C. to 85° C., 400 parts by weight of methyl isobutyl ketone, ethanol, and water was distilled out under reduced pressure (final reduced pressure: 40 kPa).

To the residual liquid, 300 parts by weight of water and 520 parts by weight of methyl isobutyl ketone were added, and 109 parts by weight of 35% hydrochloric acid was added dropwise while maintaining the temperature at 80° C. to 85° C. The resultant was stirred at this temperature for 30 minutes. After standing, an aqueous layer was removed, and a water washing operation involving addition of 250 parts by weight of water to the resulting oil layer, stirring, and removal of an aqueous layer by separation was performed twice.

Subsequently, under a reduced pressure of 45 kPa, 654 parts by weight of water and methyl isobutyl ketone was distilled out of the resulting oil layer by distillation. At 95° C. midway through the distillation, 0.3 parts by weight of seed crystals obtained by a production method known in the art was added to precipitate crystals. After this, the solution containing the crystals was cooled to 25° C. and filtered to obtain a crystalline body containing the component A.

In a container equipped with a stirrer, 100 parts by weight of the crystalline body obtained, 650 parts by weight of methyl isobutyl ketone, and 142 parts by weight of water were placed and heated to 85° C. to be dissolved, and an aqueous layer was removed by separation. A water washing operation involving addition of water to the resulting oil layer, stirring at 80° C. to 85° C., and removal of an aqueous layer by separation was performed multiple times. Subsequently, under normal pressure, 390 parts by weight of water and methyl isobutyl ketone was distilled out by distillation. At 95° C. midway through the distillation, 0.3 parts by weight of seed crystals obtained by a production method known in the art was added to precipitate crystals. After this, the crystallized solution was cooled to 25° C. and filtered, and the residue was then dried under reduced pressure to obtain 85 parts by weight of a composition for a resin raw material. The composition for a resin raw material obtained contained the component A in an amount of 99.8 area % and the component B in an amount of 0.04 area %, relative to the total amount of all components detected at a wavelength of 280 nm by high-performance liquid chromatography analysis using a UV detector.

COMPARATIVE EXAMPLE 1

In a four-necked flask, 180 parts by weight of a composition containing the component A (2,2'-bis(carboxymethoxy)-1,1'-binaphthyl) in an amount of 99.8 area %, the composition being obtained in the same manner as in Example 1, 1200 parts by weight of methyl isobutyl ketone, 31 parts by weight of ethanol, 46 parts by weight of concentrated hydrochloric acid, and 380 parts by weight of water were placed, heated to 80° C., and stirred at this temperature for 10 hours. After standing, an aqueous layer was extracted. A water washing operation involving addition of water to the resulting oil layer, stirring, and removal of an aqueous layer by separation was performed three times. Subsequently, under normal pressure, 810 parts by weight of water and methyl isobutyl ketone was distilled out of the resulting oil layer by distillation. At 95° C. midway through the distillation, seed crystals obtained by a production method known in the art were added, and precipitation of crystals was checked. After this, the solution in which crystals were precipitated was cooled to 25° C. and filtered to obtain 51.5 parts by weight of a composition for a resin raw material. The composition for a resin raw material obtained contained the component A in an amount of 95.1 area % and the component B in an amount of 4.74 area %, relative to the total amount of all components detected at a wavelength of 280 nm by high-performance liquid chromatography analysis using a UV detector.

EXAMPLE 2

Three hundred parts by weight of the composition for a resin raw material according to the present invention obtained by recrystallization in Example 1 and 100 parts by weight of the composition for a resin raw material obtained in Comparative Example 1 were mixed together. The resulting composition for a resin raw material contained the component A in an amount of 98.6 area % and the component B in an amount of 1.21 area %, relative to the total amount of all components detected at a wavelength of 280 nm by high-performance liquid chromatography analysis using a UV detector.

COMPARATIVE EXAMPLE 2

One hundred parts by weight of the composition for a resin raw material according to the present invention obtained by recrystallization in Example 1 and 100 parts by weight of the composition obtained in Comparative Example 1 were mixed together. The resulting composition for a resin raw material contained the component A in an amount of 97.5 area % and the component B in an amount of 2.37 area %, relative to the total amount of all components detected at a wavelength of 280 nm by high-performance liquid chromatography analysis using a UV detector.

<Performance Evaluation Test of Composition for Resin Raw Material>

Using the compositions for resin raw materials of Examples 1 and 2 and Comparative Examples 1 and 2 above, resins were produced according to the method described below, and the performance of the resins obtained was evaluated.

Resin Production Method

In a test tube (VIDTEC HIGH GRADE GLASS) equipped with an air cooler and a gas inlet, 73.6 parts by weight of the composition for a resin raw material of Example 1 and 26.4 parts by weight of cyclohexanedimethanol were placed, and an operation involving decompression (10 kPa >) followed by repressurization with nitrogen was performed four times to purge the test tube with nitrogen. After the flow rate of nitrogen was adjusted to 250 ml/min, the test tube was heated to 200° C. in a metal block (hot dry bath HOTB624K manufactured by AS ONE Corporation) and held there for 10 minutes. The test tube was then further heated at an increased temperature of 230° C. for 60 minutes, after which a resin was taken out on a vat and cooled.

The polyester resin obtained had a weight-average molecular weight of 4837, a glass transition temperature (Tg) of 94.1° C., and a hue (APHA) of 170.

Similarly, the compositions for resin raw materials of Example 2 and Comparative Examples 1 and 2 were used to produce resins, and the resins obtained were analyzed for their performance.

The composition ratio of the compositions for resin raw materials of Examples 1 and 2 and Comparative Examples 1 and 2 and the performance of the resins obtained are shown in Table 1 below.

TABLE 1

| Composition for resin raw material | Composition ratio | | Tg (° C.) | Hue APHA | Weight-average molecular weight |
|---|---|---|---|---|---|
| | Component A | Component B | | | |
| Example 1 | 99.8 | 0.04 | 94.11 | 170 | 4837 |
| Example 2 | 98.6 | 1.21 | 93.70 | 205 | 4619 |
| Comparative Example 2 | 97.5 | 2.37 | 92.91 | 233 | 4758 |
| Comparative Example 1 | 95.1 | 4.74 | 92.28 | 267 | 4619 |

EXAMPLE 3

Using 420 parts by weight of 1,1'-binaphthalene-2,2'-diol, 425 parts by weight of potassium carbonate, 9 parts by weight of potassium iodide, 396 parts by weight of ethyl chloroacetate, and 367 parts by weight of a 48% aqueous potassium hydroxide solution, 502 parts by weight of a composition for a resin raw material was obtained in the same manner as in Example 1 above. The composition for a resin raw material obtained contained the component A in an amount of 99.8 area % and the component B in an amount of 0.05 area %, relative to the total amount of all components detected at a wavelength of 280 nm by high-performance liquid chromatography analysis using a UV detector.

COMPARATIVE EXAMPLE 3

In the same manner as in Comparative Example 1 above, 50.5 parts by weight of a composition for a resin raw material was obtained. The composition for a resin raw material obtained contained the component A in an amount of 95.0 area % and the component B in an amount of 4.77 area %, relative to the total amount of all components detected at a wavelength of 280 nm by high-performance liquid chromatography analysis using a UV detector.

EXAMPLE 4

The composition for a resin raw material of Example 3 in an amount of 12.07 parts by weight and the composition for a resin raw material obtained in Comparative Example 3 in an amount of 4.33 parts by weight were mixed together. The resulting composition for a resin raw material contained the component A in an amount of 98.7 area % and the component B in an amount of 1.19 area %, relative to the total amount of all components detected at a wavelength of 280 nm by high-performance liquid chromatography analysis using a UV detector.

COMPARATIVE EXAMPLE 4

The composition for a resin raw material of Example 3 in an amount of 6.08 parts by weight and the composition obtained in Comparative Example 3 in an amount of 6.00 parts by weight were mixed together. The resulting composition for a resin raw material contained the component A in an amount of 97.4 area % and the component B in an amount of 2.39 area %, relative to the total amount of all components detected at a wavelength of 280 nm by high-performance liquid chromatography analysis using a UV detector.

COMPARATIVE EXAMPLE 5

The composition for a resin raw material of Example 3 in an amount of 7.59 parts by weight and the composition obtained in Comparative Example 3 in an amount of 4.50 parts by weight were mixed together. The resulting composition for a resin raw material contained the component A in an amount of 98.1 area % and the component B in an amount of 1.79 area %, relative to the total amount of all components detected at a wavelength of 280 nm by high-performance liquid chromatography analysis using a UV detector.

COMPARATIVE EXAMPLE 6

The composition for a resin raw material of Example 3 in an amount of 4.11 parts by weight and the composition obtained in Comparative Example 3 in an amount of 8.00 parts by weight were mixed together. The resulting composition for a resin raw material contained the component A in an amount of 96.7 area % and the component B in an amount of 3.15 area %, relative to the total amount of all components detected at a wavelength of 280 nm by high-performance liquid chromatography analysis using a UV detector.

Using the compositions for resin raw materials of Examples 3 and 4 and Comparative Examples 3 to 6, resins were produced according to the above resin production method, and the performance of the resins obtained was analyzed.

The composition ratio of the compositions for resin raw materials of Examples 3 and 4 and Comparative Examples 3 to 6 and the performance of the resins obtained are shown in Table 2 below.

TABLE 2

| Composition for resin raw material | Composition ratio | | Tg (° C.) | Hue APHA |
|---|---|---|---|---|
| | Component A | Component B | | |
| Example 3 | 99.8 | 0.05 | 101.3 | 177 |
| Example 4 | 98.7 | 1.19 | 101.2 | 200 |
| Comparative Example 5 | 98.1 | 1.79 | 100.2 | 217 |
| Comparative Example 4 | 97.4 | 2.39 | 100.3 | 272 |
| Comparative Example 6 | 96.7 | 3.15 | 100.2 | 273 |
| Comparative Example 3 | 95.0 | 4.77 | 99.1 | 241 |

The composition for a resin raw material according to the present invention is useful because a resin obtained using the composition for a resin raw material has greatly improved resin physical properties such as heat resistance (glass transition temperature).

In addition, when the composition for a resin raw material according to the present invention is used, a resin also having an excellent hue can be obtained in a stable manner, which is advantageous also from an industrial point of view. In optical applications, it is particularly important and significant to obtain a resin with a good hue.

That is, the provision of the composition for a resin raw material according to the present invention is very useful in that a resin having excellent resin physical properties such as heat resistance and having a good hue can be obtained in an industrially stable manner.

The invention claimed is:
1. A resin raw material composition, comprising:
    a compound represented by formula (1) as a component A, and
    a compound represented by formula (2) as a component B; and
having their composition ratios in the following ranges: composition ratios: the component A is present in an amount of 99.0 area % or more and 99.99 area % or less, and the component B is present in an amount of more than 0 area % and 1.00 area % or less, relative to a total amount of all components detected at a wavelength of 280 nm by high-performance liquid chromatography analysis using a UV detector;

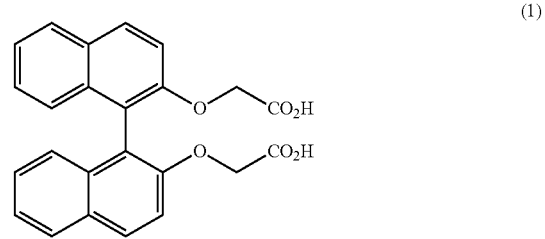

(1)

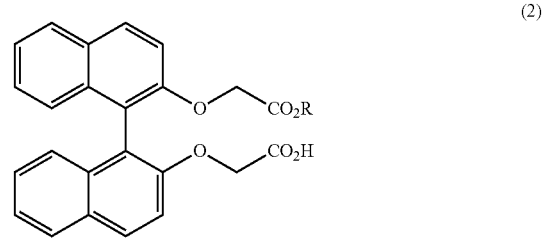

(2)

wherein R represents an alkyl group having 1 to 8 carbon atoms.

* * * * *